(12) United States Patent
Declerck

(10) Patent No.: US 9,193,051 B2
(45) Date of Patent: Nov. 24, 2015

(54) MULTIPLE STUD TENSIONING MACHINE AND METHOD FOR AUTOMATICALLY CONTROLLING THE ELONGATION OF A PLURALITY OF STUDS

(75) Inventor: Didier Declerck, Acheres (FR)

(73) Assignee: AKTIEBOLAGET SKF, Gothenburg (SE)

( * ) Notice: Subject to any disclaimer, the term of this patent is extended or adjusted under 35 U.S.C. 154(b) by 545 days.

(21) Appl. No.: 13/639,022

(22) PCT Filed: Apr. 2, 2010

(86) PCT No.: PCT/EP2010/054453
§ 371 (c)(1),
(2), (4) Date: Jan. 16, 2013

(87) PCT Pub. No.: WO2011/120589
PCT Pub. Date: Jun. 10, 2011

(65) Prior Publication Data
US 2013/0139652 A1    Jun. 6, 2013

(51) Int. Cl.
*B25B 29/02* (2006.01)
*G01N 3/08* (2006.01)
*B23P 19/06* (2006.01)
*B25B 23/14* (2006.01)
*G01B 21/32* (2006.01)

(52) U.S. Cl.
CPC .............. *B25B 29/02* (2013.01); *B23P 19/067* (2013.01); *B25B 23/14* (2013.01); *G01B 21/32* (2013.01); *G01N 3/08* (2013.01); *G01B 2210/58* (2013.01)

(58) Field of Classification Search
CPC ....... B25B 29/02; B25B 23/14; B23P 19/067; G01N 3/08; G01B 21/32; G01B 2210/58
See application file for complete search history.

(56) References Cited

U.S. PATENT DOCUMENTS

| 5,408,509 | A | 4/1995 | Ruzga et al. | |
|---|---|---|---|---|
| 8,201,315 | B2 * | 6/2012 | Monville | 29/452 |
| 8,261,421 | B2 * | 9/2012 | Monville | 29/446 |
| 8,857,532 | B2 * | 10/2014 | Wallgren | 173/1 |
| 2009/0013518 | A1 | 1/2009 | Monville | |
| 2012/0096997 | A1 * | 4/2012 | Corbett et al. | 81/473 |

FOREIGN PATENT DOCUMENTS

WO    WO2006041513 A1    4/2006

* cited by examiner

*Primary Examiner* — David B Thomas
(74) *Attorney, Agent, or Firm* — Bryan Peckjian; SKF USA Inc. Patent Dept.

(57) ABSTRACT

A multiple stud tensioner machine adapted to exert a longitudinal pre-stressing traction on a plurality of studs (2), the stud tensioner machine comprising a sensor supporting assembly (6) adapted to receive a plurality of elongation sensors (11) arranged in a row and positioning means adapted to move one (11a) of said sensors from said row into an operating engagement with one (2a) of said studs.

13 Claims, 4 Drawing Sheets

MULTIPLE STUD TENSIONING MACHINE AND METHOD FOR AUTOMATICALLY CONTROLLING THE ELONGATION OF A PLURALITY OF STUDS

CROSS-REFERENCE

This application is the U.S. national stage of International Application No. PCT/EP2010/054453 filed on Apr. 2, 2010, which is herein incorporated by reference in its entirety.

FIELD OF THE INVENTION

The present invention relates to machines and methods adapted to exert a longitudinal traction on rod like members such as threaded studs used for securing together two mechanical parts.

BACKGROUND OF THE INVENTION

The tensioning of rod like members or studs can be done by applying a tightening torque to a threaded nut resting axially on the surface of the structure to be tightened. This tightening method does not allow controlling precisely the axial force transmitted to the rod, because of frictions between the nut in contact with the surface of the part to be tightened and between the nut and the rod. Moreover, this tightening method introduces torsion residual stresses into the rod, which results in using oversize rods. In addition, such a tightening generally leads to an important risk of damage of threads of the nut and of the rod cooperating together during tightening. The surface against which the nut is resting during its rotation at the time of tightening may also be damaged.

In order to avoid these disadvantages, a rod member or a stud may be axially tensioned before fitting-up a nut on the surface of a structure to be tightened. The nut blocks the rod when the axial force applied to the rod is released. The rod is thus pre-stressed only along its axis. An actuator can be used in order to transmit an axial traction force to the rod. Thus, after the nut is positioned on a threaded portion of the rod to be tensioned, the actuator is positioned so as to surround the head portion of the rod or stud and the nut. A traction force is applied in a longitudinal direction on a threaded extension of the head part of the rod member or stud and produces an elongation of the stud. This elongation facilitates the rotation of the tightening nut adapted to cooperate with a threaded portion of the stud so as to tighten the nut. The two mechanical parts can thus be secured together by the rod member or the stud without inducing a twist or a residual torsion stress to the stud.

Large mechanical assemblies must often be maintained by several threaded rods or studs. Multiple stud tensioning machines are then used to position, screw and unscrew as well as pre-tension a plurality of threaded studs. Examples are the attachment of parts of wind turbines or of the protecting cover of nuclear power reactor shells. A number of threaded studs are usually arranged in a circular row for attachment of such kind of large mechanical assemblies.

In order to facilitate the attachment operations, for example of the protecting cover to a nuclear reactor shell, a supporting ring assembly is provided, said assembly being moved from above on the cylindrical cover installed on the nuclear power shell. The complete set of attachment studs is supported by the supporting ring which is also provided with all necessary means for screwing and unscrewing the studs as well as tensioning them in a longitudinal direction before tightening the corresponding nuts. In order to fulfill those tasks, the supporting ring is usually equipped with at least one and preferably two robot units capable of being moved along the periphery of the supporting ring for screwing, unscrewing and tightening the nuts one by one within the nuclear power shell. The longitudinal traction force for pre-stressing each individual stud before tightening is produced by a plurality of hydraulic stud tensioners, each of which is mounted on the head of a respective stud.

All the studs around the cover of the nuclear power shell must be submitted to the same longitudinal traction before the corresponding tightening nuts can be rotated so as to secure the cover to the nuclear power shell. It is therefore necessary to carefully monitor the traction force applied to all individual studs so as to guarantee an identical tension, and of course to maintain such force within specific limits depending on the tensile strength of the material used. Such monitoring is preferably made by measuring the elongation of each stud with elongation sensors, each sensor being mounted on a respective stud. The individual elongation sensors are usually mounted manually on each stud, which is particularly cumbersome. The sensors are supplied with electrical energy by electrical connections linked to a central power station. The measurement signals are transmitted from each individual elongation sensor by wire connections. Therefore, the mounting operation as well as the dismounting operation of the multiplicity of elongation sensors is particularly long and difficult.

One aim of the present invention is to avoid those drawbacks and to simplify the operations of assembling and disassembling a plurality of elongation sensors on a plurality of rod like members or studs to be tensioned in a multiple stud tensioning machine.

Another aim of the present invention is to permit a simpler monitoring of the elongation of a plurality of studs during a pre-tensioning operation.

More generally, the present invention aims at providing quicker and easier assembling and disassembling of a plurality of elongation sensors. A further aim of the invention is to provide a safer and cheaper monitoring of the elongation of a plurality of studs, during attachment of two mechanical elements together, for example, a protecting cover to a nuclear reactor shell.

SUMMARY OF THE INVENTION

In an embodiment, a multiple stud tensioner machine adapted to longitudinally tension a plurality of studs, comprises a sensor supporting assembly adapted to receive a plurality of elongation sensors arranged in a row and positioning means adapted to move one of said sensors from said row into an operating engagement with one of said studs.

All the sensors are therefore initially maintained, preferably in a stand-by state, on the supporting assembly. The assembling step of each sensor onto the corresponding stud can be made automatically thus avoiding the long and cumbersome manual operations which were previously necessary.

Each elongation sensor is preferably provided with individual wireless communication means adapted to transmit to a computer system measurement and identification signals. The wireless communication means may also receive control signals from said computer system for controlling the sensor.

No electrical wire is therefore anymore necessary which makes the assembling operations of the plurality of sensors considerably quicker and easier. The identification and measurement signals transmitted by each sensor allow the computer system to correctly monitor the tensioning operation of all the studs simultaneously. The signals are preferably sampled with an appropriate frequency, for example less than 1 s.

The machine also preferably includes indexing means capable of transmitting a position signal corresponding to the position of said stud having said sensor in operating engagement. The computer system receives such a position signal as soon as an individual sensor is placed in operating engagement with a corresponding stud. The computer system is therefore able to detect which individual sensor corresponds to which stud, so as to safely and correctly monitor the tensioning of each stud.

In an advantageous practical embodiment, the sensor supporting assembly is adapted to receive said row of sensors so that said sensors are urged by gravity toward an end position.

The sensor supporting assembly may comprise a stop means adapted to be moved between an open position and closed position in which said stop means block a sensor in said end position.

Such a structure using gravity to automatically supply the elongation sensors is particularly reliable and simple.

A movable grasping fork may be provided to receive a sensor in an intermediate position when said stop means is moved to said open position. A means for actuating a switch provided in the sensor may be mounted on the grasping fork. A seizing arm may be provided to seize said sensor in said intermediate position and to position said sensor in operating engagement with one of said studs.

The grasping fork may be withdrawn from said intermediate position as soon as the seizing arm has seized the sensor.

The seizing arm may be provided with mechanically actuatable jaws adapted to cooperate with a protruding portion of said sensor. Alternatively an electromagnetic lifting means may be provided at the end of the seizing arm for lifting the sensor and moving it in operating engagement with said stud.

After the sensor has been placed in said operating engagement with the stud, the seizing arm is moved back to its initial position and the grasping fork may also be moved back to the intermediate position so as to cooperate with the next sensor.

In a particularly simple and advantageous embodiment, the sensor supporting assembly may comprise two elongated guides adapted to receive the lateral sides of guiding plates secured to each said sensor, said elongated guides comprising a vertical portion and a curved portion ending substantially horizontally. The sensors are therefore maintained in the supporting assembly by their respective guiding plates. The gravity is sufficient to urge the queue of sensors toward the substantially horizontal end of the curved portion of the two guides where the last sensor is blocked in position by the stop means. If necessary, additional weights having the same shape as the guiding plates of the sensors may be inserted within the two elongated guides at the top of the queue so as to better urge the sensors toward the end of the curved portion.

The grasping fork is preferably adapted to receive the forward edge of the guiding plate of a sensor in said intermediate position.

The elongated guides preferably comprise electrically conducting slides cooperating with contacting portions of said plates for charging a battery mounted on each said sensor. Each individual sensor is equipped with its own battery as source of electrical energy. The batteries of the sensors maintained in the supporting assembly by their respective guiding plates, can thus be charged during the inactive time when the sensors are in stand-by state.

In an embodiment particularly adapted to a multiple stud tensioner machine for attachment of the cover dome of a nuclear power reactor shell, the sensor supporting assembly is attached to a vertical side of a robot device having at least one screwing head, said robot device being adapted to be moved over a series of studs.

In a preferred embodiment, the elongation sensor adapted to measure the deformation of a stud during a tensioning operation, comprises a rechargeable battery and also individual wireless communication means adapted to transmit to a computer system measurement and identification signals and to receive control signals from said computer system. The positioning of the sensors is thus greatly simplified since no connecting wires are necessary. This also makes possible to store the sensors in the supporting assembly before they are individually positioned on each respective stud.

According to a further aspect, the invention also relates to a method for automatically controlling the elongation of a plurality of studs during a tensioning operation of said studs. The method comprises the steps of providing a series of individual elongation sensors, positioning one of said sensors in operating engagement with each said stud prior to the tensioning operation, transmitting by wireless communication to a computer system a position signal corresponding to the position of each said stud having said sensor in operating engagement and continuously transmitting by wireless communication to the computer system, measurement and identification signals issued by each said sensor during the tensioning operation.

The method may also comprise the further step of transmitting by wireless communication from the computer system to each sensor, control signals for charging a battery included in said sensors and/or for energizing said sensors or setting said sensors in a stand-by state.

BRIEF DESCRIPTION OF THE DRAWINGS

The invention will be better understood on the basis of the description of an example which is to be considered in a non limiting way, and which is illustrated on the enclosed drawings, in which.

DETAILED DESCRIPTION OF THE INVENTION

Figure 1:
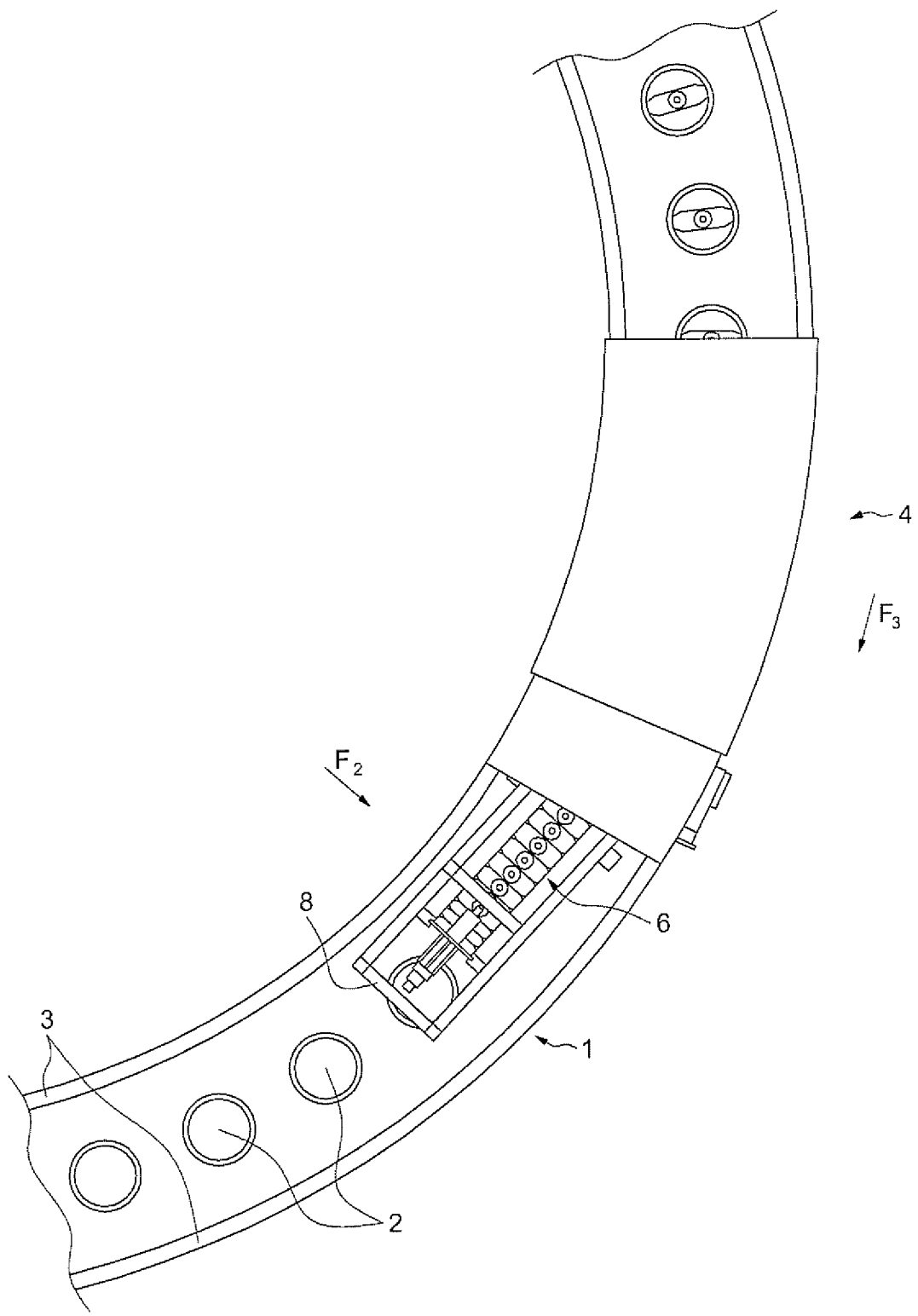
FIG. 1 is a schematic partial view of a multiple stud tensioner machine taken from above, and showing a robot with a sensor supporting assembly.
Figure 2:
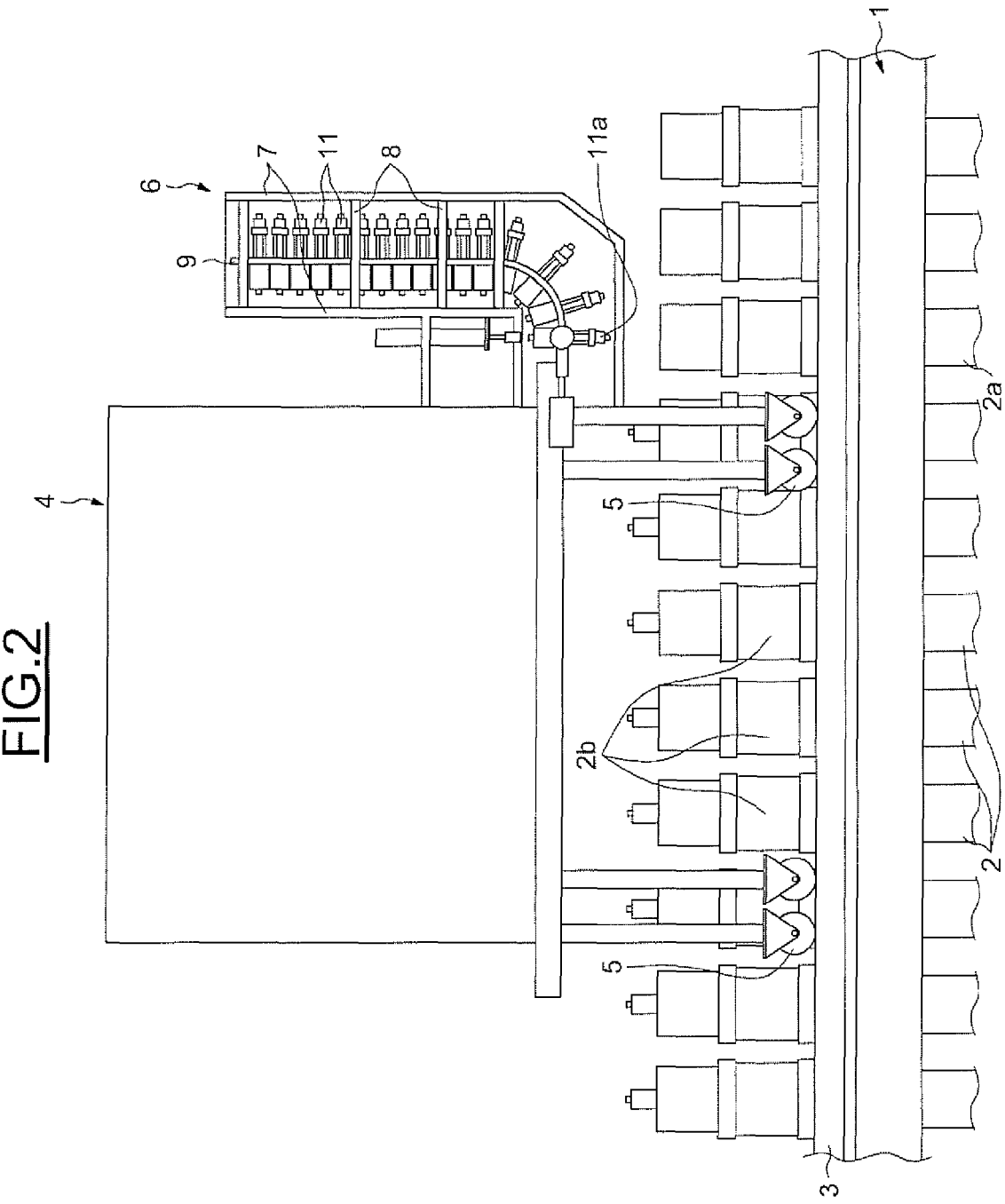
FIG. 2 is a side view taken in the direction of arrow F2 of FIG. 1, showing the robot with the sensor supporting assembly.
Figure 3:
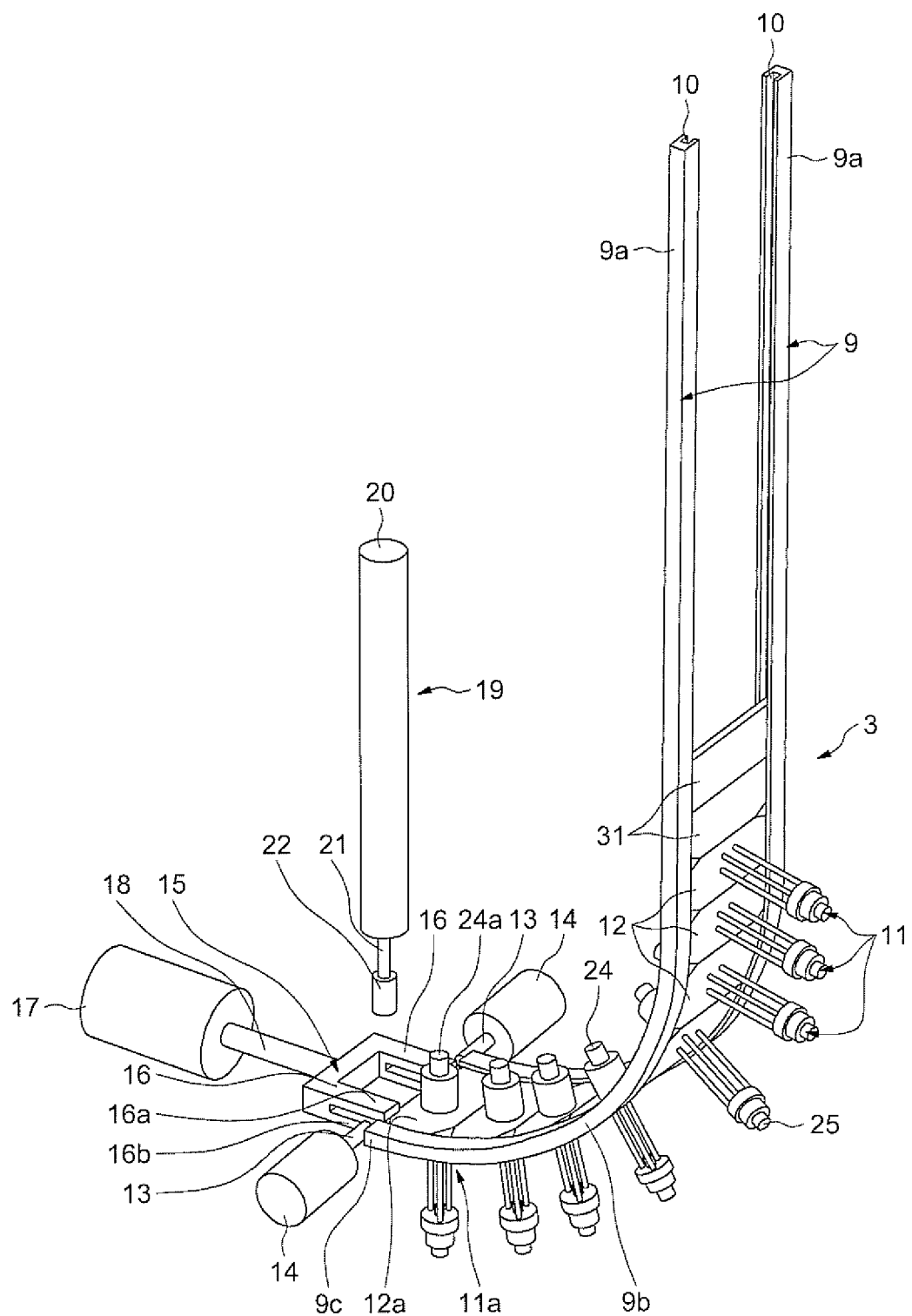
FIG. 3 is a three-dimensional view of a part of the sensor supporting assembly illustrating more particularly two elongated guides supporting a row of sensors.

As illustrated on FIGS. 1 to 3, a multiple stud tensioner machine generally comprises a main ring 1, having a plurality of holes for accommodating and supporting a plurality of studs 2 (see FIG. 2). The ring 1 has lateral rails 3 along which a robot 4 can be displaced. As illustrated on FIG. 2, the robot 4 has supporting wheels 5 cooperating with the rails 3. Each stud 2, which is to be put under traction by longitudinal tensioning, is equipped with a tensioner device 2b mounted on the head of the respective stud 2.

The robot 4 has, on one of its lateral faces, a sensor supporting assembly 6. This assembly comprises vertical elements 7 as well as horizontal elements 8, which together build a frame within which two elongated guides 9 are mounted, as best shown on FIG. 3. Said elongated guides 9 comprise a vertical portion 9a, and a curved portion 9b which terminates substantially horizontally at an end portion 9c (FIG. 3). The two guides 9 have guiding grooves 10 provided internally and facing each other. The two grooves 10 are adapted to guide a plurality of elongation sensors 11 which are ranged in a row within the two elongated guides 9.

Figure 4:
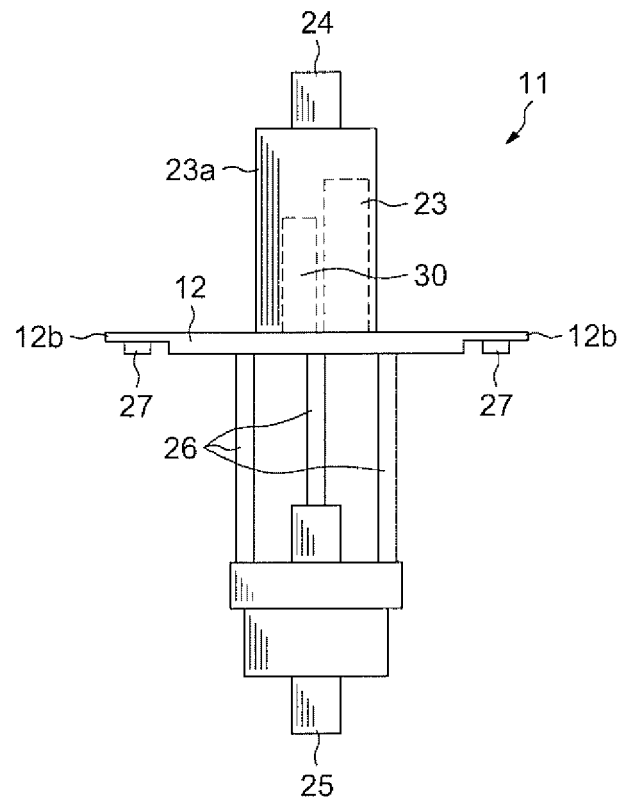
FIG. 4 shows an example of an elongation sensor which can be used in the machine of the present invention, and FIG. 5 schematically illustrates the main elements of an electronic control system for each sensor.

In the illustrated example as shown on FIG. 4, each sensor 11 comprises a guiding plate 12. The dimensions of the guiding plates 12 are such that they can be mounted in the grooves 10 of the two guides 9 and maintained in those two guides 9 for sliding movement under the effect of gravity as illustrated on FIG. 3. To this end, the two lateral end portions 12b of the guiding plates 12 are received within the respective grooves 10. Said two end portions 12b are advantageously of substantially trapezoidal shape as shown on FIG. 3, with a reduced width toward their free end.

As illustrated on FIG. 3, the sensor supporting assembly 6 comprises two stop fingers 13, which in the illustrated example, are horizontally extending fingers adapted to be moved from a closed position illustrated on FIG. 3, to an open position. In the closed position, the two fingers 13 block any further movement of the last sensor 11a, which is in an end position in the row of sensors 11. In this end position namely, the guiding plate 12a of said last sensor 11a is located substantially in the end portion 9c of the two guides 9. The sensor 11a is pushed by the row of all other sensors 11 acting by gravity and in sliding engagement with the two guides 9. The two fingers 13 in the closed position illustrated on FIG. 3 block the exit of the grooves 10 and therefore also block the plate 12a of the last sensor 11a. In said closed position, the two fingers 13 extend only in front of the grooves 10. The movement of the fingers 13 from said closed position to an open position is produced by any suitable means. As illustrated on FIG. 3, two pistons 14 are mounted horizontally on both sides of the two guides 9 at their end portion 9c. The respective rods of the two pistons 14 bear the stop fingers 13.

In the embodiment illustrated on FIG. 3, a movable grasping fork 15 is provided on the sensor supporting assembly. The fork 15 has two substantially horizontal branches 16, which are split into an upper part 16a and a lower part 16b. The gap between the lower part 16b and the upper part 16a is slightly greater than the thickness of each guiding plate 12 of the sensors 11. The overall width of the grasping fork 15 is smaller than the distance between the two guides 9. The grasping fork 15 is illustrated on FIG. 3 in a waiting position. In this position, in the illustrated example, the forward edge portion of the guiding plate 12a of the sensor 11a in the end position, is already inserted within the gap between the upper part 16a and the lower part 16b of the branches 16. The grasping fork 15 can be moved from the waiting position illustrated on FIG. 3 to a back off position by an actuating piston 17 having a movable rod 18 at the end of which the grasping fork 15 is attached. The grasping fork 15, the rod 18 and the piston 17 are mounted substantially horizontally.

When the fingers 13 are retracted to an open position, they leave passage of the guiding plate 12a, which is pushed by the guiding plates 12 of the other sensors 11. Consequently, the guiding plate 12 slides further within the gaps provided in the two branches 16 of the grasping fork 15. The sensor 11a is then in an intermediate position corresponding to the waiting position of the grasping fork 15.

In this position, the guiding plate 12a is disengaged from the grooves 10 of the guides 9 thanks to the reduced width of the trapezoidal shaped free ends of the guiding plate. The lateral edge of the guiding plate 12a is still in contact with the lateral edge of the subsequent sensor 11. The stop fingers 13 may be again moved in the closed position so as to block the guiding plate of the subsequent sensor 11 in the end position.

The grasping fork 15 having the sensor 11a between its branches 16, supports the sensor 11a in the intermediate position which is aligned with the axis of the stud 2a illustrated on FIG. 2. The axis of both the stud 2a and the sensor 11a also corresponds to the axis of a seizing arm 19 which is illustrated on FIG. 3 as a piston 20 with a movable rod 21 having at its end a mandrel 22 with gripping jaws not visible on FIG. 3. The seizing arm 19 is actuated while the guiding plate 12a of sensor 11a is still maintained in the intermediate position by the fork 15. The gripping jaws of the mandrel 22 can thus hold the sensor 11a by grasping a protruding portion 24a of sensor 11a. At that time, the fork 15 is moved to its back off position, clearing the passage of the rod 21 and allowing the seizing arm 19 to position the sensor 11a in operating engagement with the stud 2a.

As illustrated on FIG. 4, each sensor 11 has a rechargeable electrical battery 23 mounted within a box 23a on one side of the guiding plate 12. A protruding portion 24, located on the top of box 23a, can be grasped by the jaws of the mandrel 21 upon actuation of piston 20. The elongation sensor 11 has a measuring head 25 mounted at the end of supporting rods 26, for example three supporting rods at 120° from each other, attached to the guiding plate 12 on the face opposite to the box 23a of the rechargeable battery 23. The elongation of the studs 2 can be measured for example by using an elongated bar located within a hollow internal cavity of each stud 2, said cavity extending from one end to the other end of the stud 2. A nut secured at the lower end of each stud 2 serves as a support for the measuring bar. The measurement head 25 simply bears on the top of said bar and is therefore able to measure a difference in length position between the measuring bar which is not submitted to any traction, and the stud, which is submitted to a pre-tensioning traction by the corresponding tensioner device 2b.

Each elongation sensor 11 is also provided with an individual wireless communication means mounted within box 23a, and adapted to transmit measurement and identification signals, as will be explained further. The robot 4 comprises indexing means, which are not illustrated on FIG. 2, and which are capable of transmitting a position signal of the robot 4 during operation. The position signal corresponds to the position of the robot when a given sensor, for example sensor 11a, is in operating engagement with a given stud, for example stud 2a. The position signal which is transmitted by said indexing means, can be used by a computer system as will be explained further so as to precisely locate any given sensor in connection with its respective stud.

In order to charge the rechargeable batteries of each individual sensor 11, the guiding plates 12 are provided, on one of their sides, with contacting plugs 27 (FIG. 4) which are in electrical contact with the inside surface of the grooves 10. Said inside surface is made of an electrically conducting material so that the charging electrical energy can be fed through those grooves.

Figure 5:
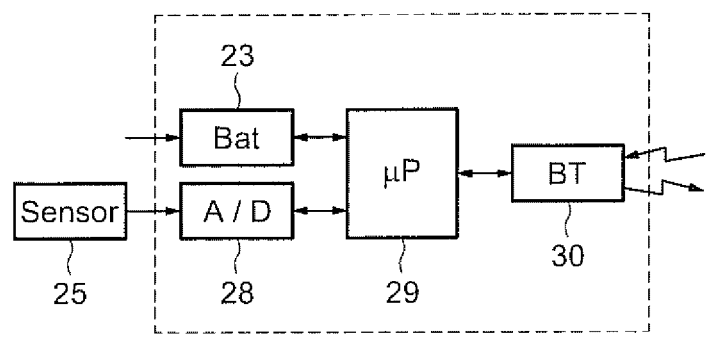

FIG. 5 illustrates schematically the main parts of a control system of a sensor 11.

The measuring head 25 of the sensor issues an analog signal which is converted into a digital signal by a converter 28. The signal is then transmitted to a microprocessor 29 incorporated into the sensor 11. After suitable conditioning, the signal is transmitted by a wireless communication device 30, for example a Bluetooth device, to a central computer system not illustrated on the figures. The electrical energy necessary for the function of the individual sensor is provided by the rechargeable battery 23. Signals from the sensor transmitted by the wireless communication device 30, can be treated by the central computer system, which is able to receive the signals transmitted by all the elongation sensors 11 during the simultaneous tensioning operation of all the studs. The central computer system may also transmit control signals to the respective sensors 11, said signals being received by the wireless communication device 30 and treated by the microprocessor 29 of each individual sensor 11. The control signals can for example set one or several sensors in operation, or, on the contrary, in a stand-by state to avoid that the individual electrical batteries of the sensors be discharged unnecessarily during the time the sensors are supported by the supporting assembly 6.

In operation, a multiple stud tensioner machine such as illustrated on FIGS. 1 to 3 is able to efficiency control the elongation of all the studs during the tensioning operation. The elongation sensors which are preferably in a stand-by state, are supported by the sensor supporting assembly attached to the robot unit 4 as shown on FIG. 1. The robot unit 4 can be moved along the periphery of ring 1 so as to position an individual elongation sensor 11 on the head of each stud. The robot unit 4 is moved step by step in the direction of arrow F3. Each time the robot unit 4 reaches a position corresponding to a given stud, the movement of the robot unit 4 is stopped and an individual elongation sensor 11 is positioned on the corresponding stud as previously explained. The central computer system receives a signal indicating the exact position of the stud and the exact correspondence with a given elongation sensor, which is identified by a specific code.

In a preferred embodiment, the grasping fork 15 is provided with means capable of energizing the elongation sensor as soon as it is moved in engagement with said grasping fork. As an example, the grasping fork may have a permanent magnet which is capable of actuating an ILF type switch provided on the sensor. The corresponding sensor is then in an active state allowing transmission by wireless communication of the identification signal corresponding to the given sensor and the subsequent measurement of the elongation of the corresponding stud.

Due to the fact that each sensor has its own electrical energy source and is able to transmit and receive signals by wireless communication, the entire operation of mounting of the multiple sensors becomes particularly quick and easy. The sensor supporting assembly in which the sensors are kept in a vertical row and simply moved by gravity allows a particularly simple function. For the case the last sensors in the supporting assembly would not slide until the end position of the two guides 9, particularly toward the end portion 9c, it is advisable to add supplemental weights 31 having the shape of guiding plates 12 on the top of the row of sensors as illustrated on FIG. 3.

The present invention provides therefore a more simple and efficient way of mounting elongation sensors on a plurality of studs to be tensioned in a multiple stud tensioning machine. The invention also allows an easy monitoring of the elongation of the plurality of studs during the pre-tensioning operation.

The invention claimed is:

1. A multiple stud tensioner machine adapted to exert a longitudinal pre-stressing traction on a plurality of studs, the multiple stud tensioner comprising,
    a sensor supporting assembly adapted to receive a plurality of elongation sensors arranged in a row, and
    positioning means adapted to move one of the sensors from the row into an operating engagement with one of the studs.

2. The multiple stud tensioner machine of claim 1, wherein each elongation sensor is provided with individual wireless communication means adapted to transmit to a computer system, measurement and identification signals and to receive control signals from the computer system.

3. The multiple stud tensioner machine of claim 1, further comprising indexing means capable of transmitting a position signal corresponding to the position of the stud having the sensor in operating engagement.

4. The multiple stud tensioner machine of claim 1, wherein the sensor supporting assembly is adapted to receive the row of sensors so that the sensors are urged by gravity toward an end position; and the sensor supporting assembly includes a stop means adapted to be moved between an open position and a closed position wherein the stop means block a sensor in the end position.

5. The multiple stud tensioner machine of claim 4, wherein a movable grasping fork is adapted to receive the sensor in an intermediate position when the said stop means is moved to the open position; and a seizing arm is adapted to seize the sensor in said intermediate position and to position the sensor in operating engagement with one of the studs.

6. The multiple stud tensioner machine of claim 5, wherein the seizing arm is provided with at least one of mechanically actuatable jaws and electromagnetic means adapted to cooperate with a protruding portion of the sensor.

7. The multiple stud tensioner machine of claim 1, wherein the sensor supporting assembly provides two elongated guides adapted to receive the lateral sides of guiding plates secured to each sensor, the elongated guides having a vertical portion and a curved portion ending substantially horizontally.

8. The multiple stud tensioner machine of claim 5, wherein said elongated guides include electrically conducting slides cooperating with contacting portions of the plates for charging a battery mounted on each the sensor.

9. The multiple stud tensioner machine of claim 1, wherein the sensor supporting assembly is attached to a vertical side of a robot unit having at least one screwing head, the robot unit being adapted to be moved over a series of studs.

10. An elongation sensor adapted to measure the deformation of a stud during a tensioning operation, the elongation sensor comprising, a guiding plate configured to engage a sensor supporting assembly that is configured to place the elongation sensor into the stud, a rechargeable battery, mounted within a box, the box located on the guiding plate and having a length and a width less than the guiding plate such that the box does not engage the sensor supporting assembly, wherein the guiding plate comprises electrical contacting portions for charging the rechargeable battery wherein the electrical contacting portions are not enclosed such that the electrical contacting portions are configured to electrically contact a surface neither on nor within the elongation sensor, and individual wireless communication means adapted to transmit to a computer system, measurement and identification signals and to receive control signals from the computer system.

11. The elongation sensor of claim 10, wherein the guiding plate further comprises two end portions having a trapezoidal shape and a thickness less than a guiding plate thickness, the electrical contact portions located on a side of the end portions and configured to contact the sensor supporting assembly.

12. A method for automatically controlling the elongation of a plurality of studs during a tensioning operation of said studs, comprising the steps of:
    providing a series of individual elongation sensors (11), positioning one of said sensors in operating engagement with each said stud (2) prior to the tensioning operation, transmitting by wireless communication to a computer system a position signal corresponding to the position of each the stud having the sensor in operating engagement and continuously transmitting by wireless communication to the computer system, measurement and identification signals issued by each the sensor during the tensioning operation.

13. The method of claim 12, further comprising the step of transmitting by wireless communication from the computer system to each sensor, control signals for charging a battery included in the sensors and/or for energizing the sensors or setting the sensors in a stand-by state.

\* \* \* \* \*